United States Patent [19]

Peglion et al.

[11] Patent Number: 5,733,908
[45] Date of Patent: Mar. 31, 1998

[54] TETRACYCLIC 1,4-OXAZINE COMPOUNDS

[75] Inventors: Jean-Louis Peglion, Le Vesinet; Bertrand Goument, Viroflay; Jean-Christophe Harmange, Saint Germain En Laye; Mark Millan, Le Pecq; Valérie Audinot, Poissy, all of France

[73] Assignee: Adir Et Compagnie, Courbevoie, France

[21] Appl. No.: 745,212

[22] Filed: Nov. 8, 1996

[30] Foreign Application Priority Data

Nov. 9, 1995 [FR] France ............... 95 13270

[51] Int. Cl.$^6$ ............... A61K 31/535; C07D 265/34; C07D 498/00
[52] U.S. Cl. ............... 514/229.5; 544/99
[58] Field of Search ............... 544/99; 514/229.5

[56] References Cited

U.S. PATENT DOCUMENTS 5,593,989 1/1997 Peglion et al. ............... 514/229.5

OTHER PUBLICATIONS

Millan et al. European Journal of Pharmacology 260 (1994) R3–R5.
Waters et al. J. Neural Transm [GenSect] (1993) 94:11–19.
Caine et al. Science, vol. 260, 1814–1816, 18 Jun. 1993.
Sokoloff et al. Nature, vol. 347, 146–151, Sep. 13, 1990.
The Merck Manual of diagnosis and therapy (seventh edition) 1992.

*Primary Examiner*—Mukund J. Shah
*Assistant Examiner*—Bruck Kifle
*Attorney, Agent, or Firm*—The Firm of Gordon W. Hueschen

[57] ABSTRACT

New compounds of formula:

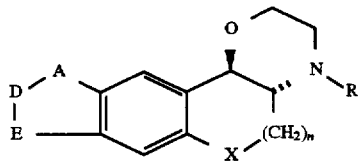

wherein:

A—D—E, X, n and R are as defined in the description, in racemic form and in the form of optical isomers, and their addition salts with pharmaceutically acceptable acids.

Those compounds may be used as medicaments.

4 Claims, No Drawings

TETRACYCLIC 1,4-OXAZINE COMPOUNDS

The present invention relates to new tetracyclic 1,4-oxygine compounds, a process for their preparation and pharmaceutical compositions containing them.

It relates more especially to tetracyclic 1,4-oxazine compounds of formula I:

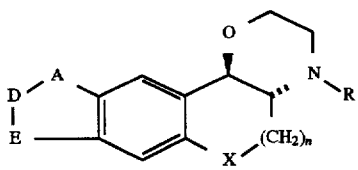

wherein:

—A—D—E— represents:

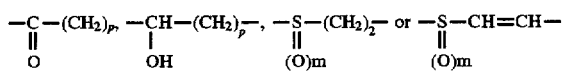

wherein:

p represents 2 or 3 and
m represents zero, 1 or 2;

X represents:
a $CH_2$ group and in addition,
when —A—D—E— represents

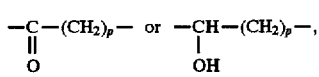

X may also represent an oxygen atom;

n represents:
zero or 1 when X represents a $CH_2$ group and solely 1 when X represents an oxygen atom;

R represents:
a hydrogen atom or
a ($C_1$–$C_{10}$)alkyl, ($C_3$–$C_{10}$)alkenyl or ($C_3$–$C_{10}$)alkynyl radical, each in straight or branched chain and each optionally substituted by one or more cycloalkyl radicals having from 3 to 8 carbon atoms, or by an aryl radical selected from the radicals phenyl, thienyl and pyridyl, each of which is optionally substituted by one or more substituents selected from halogen atoms, the hydroxy radical, and alkyl and alkoxy radicals each having from 1 to 6 carbon atoms in straight or branched chain.

The compounds of the invention have a trans ring junction between the 1,4-oxazine ring and the ring adjacent thereto.

The presence of asymmetric carbon atoms implies that the compounds of the invention exist in the form of a racemic mixture and in the form of optical isomers, which are also included in the present invention.

In addition, the compounds of formula I may form with pharmaceutically acceptable inorganic or organic acids physiologically tolerable acid addition salts, which also form part of the present invention.

The closest prior art to the present invention is constituted by:

the benzopyran compounds of formula:

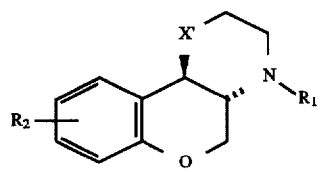

wherein:
$R_2$ neither includes nor suggests the group A—D—E defined above, and
X' represents:
an oxygen atom (see EP 0 246 633) or
a $CH_2$ group (see EP 0 161 218)
and also the compounds of formula:

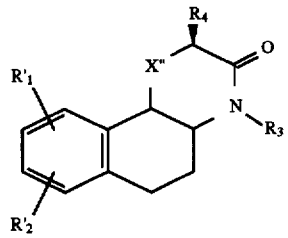

described in the application WO 93.24471.

Those substances act on the $D_2$ dopaminergic receptor, to which they bind very strongly. As a result they can be used, when they are blockers of that $D_2$ receptor, in the treatment of schizophrenia and, when they are activators of that receptor, in the treatment of Parkinson's disease.

However, their strong activity in respect of the $D_2$ receptor means that their use brings about troublesome side effects, such as tardive dyskinesia, hyperprolactinaemia and amenorrhoea in the case of the blocking agents, and cardiovascular and motor effects in the case of the activators.

The recent discovery of a new dopamine receptor, called the $D_3$ receptor, the concentration of which is very significant in the limbic system but very low in the nigrostriated nucleus and in the lactotrophic cells, encourages research into new medicaments that act on the dopaminergic system but that have as a preferential target the $D_3$ receptor and are thus exempt from the side effects typically associated with activity at the $D_2$ receptor as mentioned above.

Studies carded out in vitro (binding to cloned $D_2$ and $D_3$ receptors) with the compounds of the present invention demonstrate that the latter behave like figands that have a high affinity for the $D_3$ dopaminergic receptor while having little affinity for the $D_2$ dopaminergic receptor.

That selectivity makes the compounds of the present invention valuable especially for use as medicaments that act on the dopaminergic system without causing the undesirable effects of $D_2$ ligands. That activity of the compounds of the present invention has also been demonstrated in vivo by means of the reversal test of hypothermia induced by the prototype $D_3$ agonist (7-OH-DPAT) according to the method of M. J. Millan, Eur. J. Pharmacol. (1994), 260, $R_3$–$R_5$.

The compounds of the present invention thus differ from the products of the prior art not only in their chemical structure but also in their pharmacological activity, which allows them to exert a beneficial effect when used in the treatment of Parkinson's disease [J. Neur. Transm., (1993), 94, 11–19], memory disorders [Nature, (1990), 347, 146–151], drag abuse [Science, (1993), 260, 1814], depression and psychoses.

The present invention relates also to a process for the preparation of compounds of formula I which is characterised in that:

a primary amine of formula II:

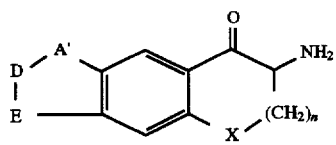

(II)

wherein:

X and n are as defined hereinbefore and
—A'—D—E— represents: —(CH$_2$)$_3$—, —(CH$_2$)$_4$—, —S—(CH$_2$)$_2$— or —S—CH=CH— is reacted with a halogenated compound of formula III:

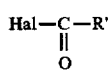

(III)

wherein:

Hal represents a chlorine or bromine atom and
R' represents:
  a cycloalkyl radical having from 3 to 8 carbon atoms; an aryl radical selected from the radicals phenyl, thienyl and pyridyl, each of which is optionally substituted by one or more substituents selected from halogen atoms, the hydroxy radical, and alkyl and alkoxy radicals each having from 1 to 6 carbon atoms in straight or branched chain, or
  a (C$_1$–C$_9$)alkyl, (C$_2$–C$_9$)alkenyl or (C$_2$–C$_9$)alkynyl radical, each in straight or branched chain and each optionally substituted by one or more cycloalkyl radicals having from 3 to 8 carbon atoms, or by an aryl radical selected from the radicals phenyl, thienyl and pyridyl, each of which is optionally substituted by one or more substituents selected from halogen atoms, the hydroxy radical, and alkyl and alkoxy radicals each having from 1 to 6 carbon atoms in straight or branched chain, to obtain a compound of formula IV:

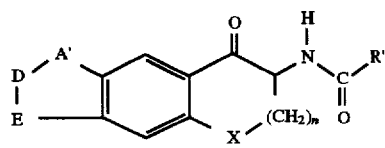

(IV)

wherein A'—D—E, X, n and R' are as defined hereinbefore, which compound of formula IV is then reduced, either with lithium aluminium hydride at approximately –78° C. in tetrahydrofuran, or with sodium borohydride in ethanol, to obtain the trans-amido-alcohol of formula V:

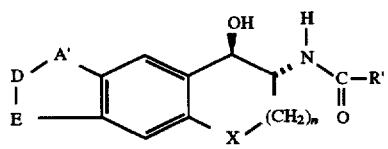

(V)

wherein A'—D—E, X, n and R' are as defined hereinbefore, which is then reduced at room temperature by means of lithium aluminium hydride in tetrahydrofuran to obtain a trans-amino-alcohol of formula VI:

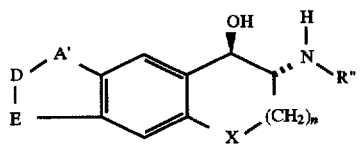

(VI)

wherein:

A'—D—E, X and n are as defined hereinbefore, and R" has the same meanings as R with the exception of hydrogen and methyl;

which compound of formula VI is treated with an acid halide of formula VII:

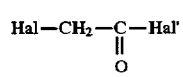

(VII)

wherein Hal and Hal', which are identical or different, each represents a chlorine or bromine atom, to obtain a compound of formula VIII:

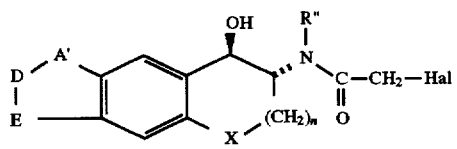

(VIII)

wherein:

A'—D—E, X, n and R" are as defined hereinbefore;

which is treated with an alkali metal hydride, such as, for example, sodium hydride, to obtain a compound of formula IX:

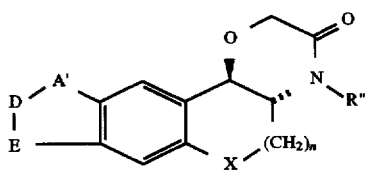

(IX)

wherein A'—D—E, X, n and R" are as defined hereinbefore, which compound of formula IX is then treated with borane-dimethyl sulphide to yield a compound of formula X:

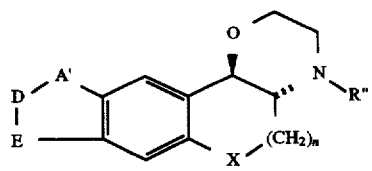

(X)

wherein

A'—D—E, X, n and R" are as defined hereinbefore, and, when R" represents a benzyl radical, the corresponding compound of formula XI:

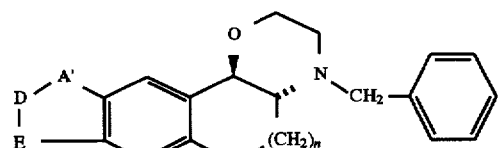

(XI)

wherein A'—D—E, X and n are as defined hereinbefore is debenzylated to obtain a compound of formula XII:

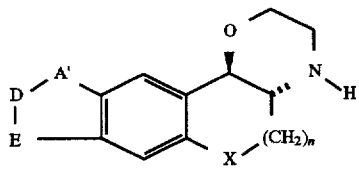
(XII)

wherein A'—D—E, X and n are as defined hereinbefore, which in turn is treated with a methylation agent to yield a compound of formula XIII:

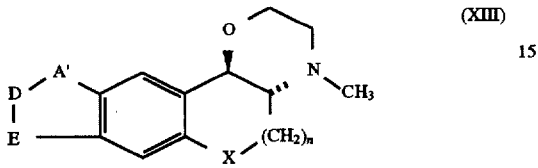
(XIII)

wherein A'—D—E, X and n are as defined hereinbefore, and the compounds of formula X, XII and XIII which, taken together, form the totality of the compounds of formula I':

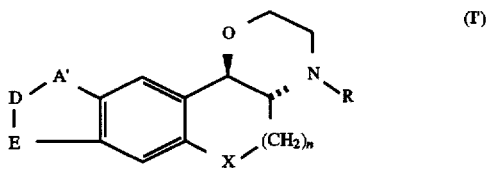
(I')

wherein A'—D—E, X, n and R are as defined hereinbefore, are oxidised by means:

either of Jones reagent or 2,3-dichloro-5,6-dicyano-1,4-benzoquinone in acetic acid and water in the case where —A'—D—E— represents —(CH$_2$)$_3$— or —(CH$_2$)$_4$—, or of hydrogen peroxide or meta-chloroperbenzoic acid in the case where —A'—D—E— represents —S—(CH$_2$)$_2$— or —S—CH=CH—, to obtain the compounds of formula I":

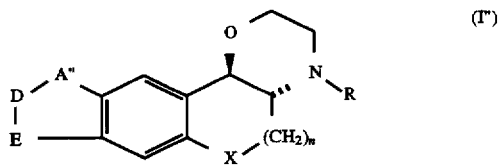
(I")

wherein:

X, n and R are as defined hereinbefore and —A"—D—E— represents the group:

—C—(CH$_2$)$_p$—,   —S—(CH$_2$)$_2$—   or   —S—CH=CH—
‖                    ‖                       ‖
O                    (O)$_{m'}$              (O)$_{m'}$ wherein:

p is as defined hereinbefore and m' represents 1 or 2; and, in the case where —A"—D—E— represents —C—(CH$_2$)$_p$—,
‖
O the corresponding compounds [that is to say the compounds corresponding more specifically to formula I"a:

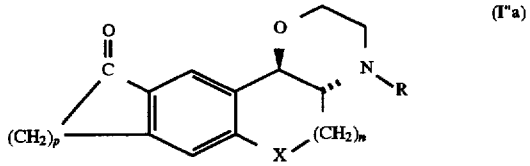
(I"a)

wherein p, X, n and R are as defined hereinbefore] are reduced with sodium borohydride or with lithium aluminjure hydride to obtain the compounds of formula I"b:

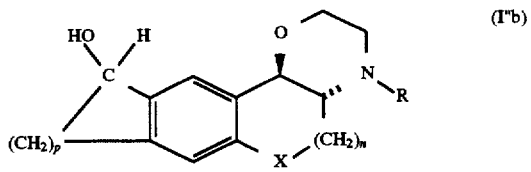
(I"b)

wherein p, X, n and R are as defined hereinbefore.

The totality of the compounds of formula I' wherein —A'—D—E— represents solely —S—(CH$_2$)$_2$ or —S—CH=CH— and of the compounds of formula I' and I'b form the totality of the compounds of formula I.

The optically active forms of the compounds of formula I were obtained either from the optically active forms of the starting materials of formula II, or by splitting the racemic forms of the compounds of formula I, according to methods known from the literature.

The salts of the compounds of formula I with pharmaceutically acceptable acids were obtained according to conventional methods as indicated in the Examples hereinafter.

The starting materials of formula II are either known products or products obtained from known substances according to known methods as described hereinafter in Preparations 1 and 2.

The present invention relates also to pharmaceutical compositions comprising as active ingredient a compound of formula I or a physiologically tolerable salt thereof, mixed with or associated with one or more appropriate pharmaceutical excipients.

The pharmaceutical compositions so obtained are generally presented in dosage form containing from 0.5 to 25 mg of active ingredient. They may, for example, be in the form of tablets, dragées, gelatin capsules, suppositories or injectable or drinkable solutions and may be administered by the oral, rectal or parenteral mute, depending on the forms used.

The dosage varies in accordance with the age and weight of the patient, the administration route, and associated treatments, and ranges from 0.5 to 25 mg of active ingredient from 1 to 3 times per day.

The following Examples, which are given as non-limiting examples, illustrate the present invention.

The melting points were determined either using a Kofler hot plate (K), or a hot plate under a microscope (MK).

SYNTHESIS OF THE STARTING MATERIALS

The starting materials used in the following Examples were prepared as follows:

Preparation 1:

3-Amino-4-oxocyclopenta[g]-3,4-dihydro-2H-benzopyran hydrochloride

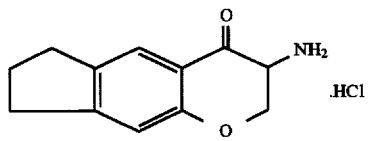

Step A: 3-(Indan-5-yloxy)propionitrile 40.2 g of indan-5-ol, 3 ml of a 40 % solution of Triton B in methanol and 200 ml of freshly distilled acrylonitrile are mixed at room temperature. The mixture is heated at reflux for 48 hours, then as much acrylonitrile as possible is evaporated off. The residue is taken up in ethyl acetate, washed with N sodium hydroxide solution, with N hydrochloric acid and with a saturated aqueous solution of sodium chloride. The organic phase is dried over magnesium sulphate and concentrated, and then the residue is recrystallised from diisopropyl ether to yield 40 g of the desired compound.

M.p. (K): 66° C., Yield: 71%.

Step B: 3-(Indan-5-yloxy)propionic acid 20.9 g of the compound obtained in the preceding Step in 33 ml of concentrated sulphuric acid and 44 ml of water are heated at reflux for 4 hours. 250 ml of water are then added and the whole is cooled in an ice bath. The solid formed is filtered off, washed with water and dried in vacuo, and then recrystallised from diisopropyl ether to yield 11.4 g of the desired compound.

M.p: (K): 146° C., Yield: 50 %.

Step C: 4-Oxocyclopenta[g]-3,4-dihydro-2H-benzopyran 2 drops of dimethylformamide are added and then, dropwise, in the course of 15 minutes, 9.4 ml of oxalyl chloride are added, to 14.8 g of the compound obtained in the preceding Step in 145 ml of chloroform at 0° C. The whole is stirred for 2 hours at room temperature, is then brought to 0° C. and, in the course of 20 minutes, 14.3 g of aluminium chloride are added thereto in portions. The whole is stirred for the night at room temperature and is then hydrolysed by pouring into 500 ml of ice-cold 3N hydrochloric acid and extracted with dichloromethane. The organic phases are washed with N hydrochloric acid, with N sodium hydroxide solution and with water, and then dried over magnesium sulphate and concentrated. The residue is chromatographed on silica (eluant: dichloromethane) to yield 12.4 g of the desired compound in the form of an oil.

Yield: 81%.

Step D: 4-Hydroxyiminocyclopenta[g]-3,4-dihydro-2H-benzopyran 16.2 g of the compound of the preceding Step, 25.1 g of hydroxylamine hydrochloride and 25.1 g of sodium acetate in 172 ml of ethanol are heated at reflux for 1 hour. The solvent is evaporated off, and the residue is taken up in dichloromethane and washed with water. After drying over magnesium sulphate, evaporation and then recrystallisation from ethanol, 11.3 g of the desired compound are obtained.

M.p. (K): 72°–76° C., Yield: 65 %.

Step E: 4-p-Toluenesulphonyloxyiminocyclopenta[g]-3,4-dihydro-2H-benzopyran 12.6 g of tosyl chloride are added in portions to 11.2 g of the compound obtained in the preceding Step in 55 ml of pyridine at 0° C. The whole is stirred for 3 hours at 0° C., and then for 20 hours at room temperature, and is subsequently poured into 600 ml of water and extracted with ether. The combined ethereal phases are washed with water, with 0.5N sulphuric acid and with water, and are then dried over magnesium sulphate and concentrated to yield 19.1 g of the desired compound.

M.p. (K): 134° C., Yield: 97 %.

Step F: Title product 19 g of the compound obtained in the preceding Step in 69 ml of benzene are added to sodium ethanolam in ethanol (prepared from 1.4 g of sodium and 53 ml of anhydrous ethanol) at 0° C. After 6 hours' stirring at room temperature, then leaving for the night in a refrigerator, the solid formed is filtered off and washed with benzene. The filtrates are poured into 120 ml of 4N hydrochloric acid while stirring vigorously. The solid formed is filtered off and dried in vacuo to yield 8.55 g of the desired compound in the form of the hydrochloride.

M.p. (K) >260° C., Yield: 67%.

Preparation 2:

2,3,5,6,7,8-Hexahydro-8-oxo-7-aminonaphtho[2,3-b]thiophene hydrochloride

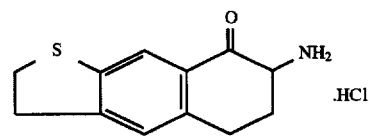

Step 1: 2,3,5,6,7,8-Hexahydro-8-hydroxyiminonaphtho[2,3-b]thiophene

In a 250 ml two-necked flask fitted with a mechanical stirrer, 10.2 g (50 mmol) of 2,3,5,6,7,8-hexahydro-8-oxonaphtho[2,3-b]thiophene (prepared according to W. Carrothers et al; Chem. Soc., 1962, p. 704-708); 14.6 g (210 retool) of NH2OH/HCl and 14.6 g (177 retool)of sodium acetate are dissolved in 100 ml of ethanol and the mixture is heated at reflux for one hour. After returning to room temperature, the reaction mixture is taken up in 100 ml of CH$_2$Cl$_2$ and then filtered. The filtrate is concentrated. The residue is taken up in 200 ml of CH$_2$C12 and 100 ml of water. The phases are separated, and the organic phase is washed four times with 50 ml of water each time, dried over magnesium sulphate and concentrated in vacuo to yield 9.96 g of the expected product. Yield: 91%.

Step 2: 2,3,5,6,7,8-Hexahydro-8-p-toluenesulphonylhydroxyiminonaphtho[2,3-b]thiophene In a 250 ml two-necked flask fitted with a mechanical stirrer and a nitrogen inlet, 9.9 g (45 mmol) of the product obtained in Step 1 are dissolved in 55 ml of pyridine. The solution is cooled to 0° C. and 12.9 g (68 retool) of tosyl chloride are added in portions. After 18 hours' stirring at room temperature, the reaction mixture is poured into an aqueous solution of NaHCO$_3$ (200 ml) at 0° C. The aqueous phase is extracted four times with CH$_2$Cl$_2$. The organic phases are combined, washed twice with 1N HCl, dried over magnesium sulphate and concentrated in vacuo to yield 15.4 g of the expected product. Yield: 92 %.

Step 3: Title product

In a 250 ml three-necked flask fitted with a mechanical stirrer and a nitrogen inlet, 0.58 g (25 mmol) of sodium is added in portions to 21 ml of dry ethanol. The sodium ethanolate solution thus obtained is cooled to 0-5° C. and 7.8 g (21 mmoD of the product obtained in Step 2 dissolved in 54 ml of benzene are added. After 18 hours' stirring at room temperature, the reaction mixture is filtered and the flitrate is poured into an aqueous solution of 4N HCl (100 ml) at 0° C. The solution thus obtained is concentrated in vacuo without going to dryness and the brownish solid is filtered off and then dried to yield 3.3 g of the expected product. Yield: 62 %.

Example 1:

Trans-3,4,4a,11b-tetrahydro-10-oxocyclopenta[g]-1,4-oxazino[5,6-c]-4-propyl-5H-benzopyran and its hydrochloride

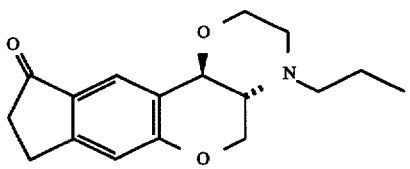

Step A: 3-Propionylamino-4-oxocyclopenta[g]-3,4-dihydro-2H-benzopyran 260 ml of an aqueous 5 % sodium carbonate solution and then 4.6 ml of propionyl chloride are added to 8.45 g of the compound obtained in Preparation 1 suspended in 260 ml of ethyl acetate at room temperature. The whole is stirred for the night at room temperature, the phases are separated, and the aqueous phase is back-extracted with dichloromethane. The combined organic phases are dried over magnesium sulphate and concentrated to yield 8.55 g of the desired compound.

M.p. (K): 159° C., Yield: 94 %.

Step B: 3-Propionylamino-4-hydroxycyclopenta[g]-3,4-dihydro-2H-benzopyran 1.3 g of sodium borohydride are added in portions to 8.5 g of the compound obtained in the preceding Step in 165 ml of ethanol at room temperature, and the whole is stirred for 24 hours at room temperature and then evaporated to dryness. The residue is taken up in water and extracted with dichloromethane. The organic phases are dried over magnesium sulphate and concentrated to yield 8.4 g of the desired compound (cis/trans: 25/75). Yield: 98 %.

Step C: Trans-3-propylamino-4-hydroxycyclopenta[g]-3,4-dihydro-2H-benzopyran 8.3 g of the compound obtained in the preceding Step suspended in 90 ml of tetrahydrofuran are added in portions in the course of 30 minutes to 3.02 g of lithium aluminium hydride in 45 ml of tetrahydrofuran at room temperature. The whole is stirred for the night at room temperature and then for I hour at reflux, cooled in ice and hydrolysed with 2.1 ml of water, followed by 1.67 ml of 20 % sodium hydroxide solution and then 7.6 ml of water, and stirred at room temperature for 3 hours. The salts are filtered off and washed with tetrahydrofuran and the flitrates are concentrated. The residue thus obtained is recrystallised twice from ethyl acetate to yield 3.6 g of the desired compound (100 % trans). M.p. (K): 152° C., Yield: 46 %.

Step D: Trans-3-(N-propyl-N-chloroacetylamino)-4-hydroxycyclopenta[g]-3,4-dihydro-2H-benzopyran 210 ml of an aqueous 5 % sodium carbonate solution and then 1.67 ml of chloroacetyl chloride are added to 3.5 g of the compound obtained in the preceding Step suspended in 210 ml of ethyl acetate at room temperature. The whole is stirred for the night at room temperature, the phases are separated, and the aqueous phase is back-extracted with dichloromethane. The combined organic phases are dried over magnesium sulphate and concentrated to yield 4.6 g of the desired compound. Quantitative yield.

Step E: Trans-3,4,4a,11b-tetrahydro-3-oxocyclopenta[g]-1,4-oxazino[5,6-c]-4-propyl-5H-benzopyran 4.5 g of the compound obtained in the preceding Step dissolved in 70 ml of tetrahydrofuran and 20 ml of acetonitrile are added dropwise in the course of 10 minutes to 0.84 g of sodium hydride in 25 ml of tetrahydrofuran at room temperature. The whole is stirred at room temperature for 24 hours then, at 0° C., excess sodium hydride is destroyed by the addition of 9 ml of methanol. The whole is evaporated to dryness, taken up in dichloromethane and washed with water, the phases are separated, and the aqueous phase is back-extracted with dichloromethane. The combined organic phases are dried over magnesium sulphate and concentrated to yield 3.9 g of the desired compound. M.p. (K): 160° C., Yield: 97 %.

Step F: Trans-3,4,4a, 11b-tetrahy.drocyclopenta[g]- 1,4-oxazino[5,6-c]-4-propyl-5H-benzopyran 12.5 ml of borane-dimethyl sulphide are added dropwise to 3.8 g of the compound obtained in the preceding Step in 150 ml of tetrahydrofuran at room temperature. The whole is heated at reflux for the night, cooled and solvolysed with 26 ml. of methanol, and is then heated at reflux again for 3 hours before evaporation to dryness. The residue thus obtained is chromatographed on silica (eluant: dichloromethane/ethyl acetate 94/6) to yield 2.58 g of the desired compound. M.p. (K): 82° C., Yield: 79 %.

Step G: Title product 2.86 g of 2,3-dichloro-5,6-dicyano-1,4-benzoquinone are added in portions to 1.16 g of the compound obtained in the preceding Step dissolved in 150 ml of acetic acid and 30 ml of water, and then the whole is heated at reflux for 5 hours. After evaporation to dryness, the residue is taken up in dichloromethane and filtered over Celite. After evaporation, the residue is chromatographed on silica (eluant: dichloromethane/ethyl acetate) to yield 0.37 g of free base.

M.p. (MK): 122-123° C., after recrystallisation from ethyl acetate.

That product is taken up in an ether/tetrahydrofuran mixture, 1.1 equivalents of 3.7N ethereal hydrogen chloride are added thereto and the solid formed is filtered off, washed with ether and dried in vacuo to yield 0.38 g of the title product in the form of the hydrochloride. M.p.(MK): 210–213° C., Yield: 28 %.

Example 2:

Trans-3,4,4a,5,6,8,9,11b-octahydrothieno[2,3-b]-1,4-oxazino[3,2-h]-4-propyl-2H-naphthalene and its hydrochloride

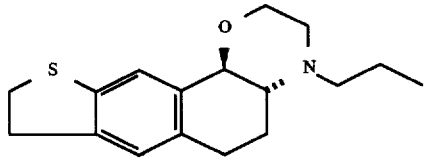

Step 1: 2,3,5,6,7,8-Hexahydro-8-oxo-7-propi0nylaminonaphtho[2,3-b]thi.ophene

In a 250 ml three-necked flask fitted with a mechanical stirrer, 2.56 g (10 retool) of the product obtained in Preparation 2 are suspended in 74.5 ml of ethyl acetate. 74.5 ml of an aqueous 5 % $Na_2CO_3$ solution are added at room temperature and the two-phase mixture is stirred vigorously until dissolution is complete. 1.3 ml (15 retool) of propionyl chloride are added to that two-phase solution at room temperature. After 5 hours' stirring at room lo temperature, the organic and aqueous phases are separated and the aqueous phase is extracted three times with ethyl acetate.

The organic phases are combined, dried over magnesium sulphate and concentrated to yield 2.47 g of the expected product. Yield: 90 %.

Step 2: Trans-2,3,5,6,7,8-hexahydro-8-hydroxy-7-propionylaminonaphtho[2,3-b]thiophene In a 4-liter three-necked flask fitted with a mechanical stirrer and a nitrogen inlet, 3.8 g (99.5 mmol) of AlLiH$_4$ are suspended in 850 ml of dry tetrahydrofuran. At −78° C., 22.8 g (253 retool) of the product obtained in Step 1 dissolved in 1,060 ml of dry tetrahydrofuran are slowly added while maintaining the temperature of the reaction mixture below −70° C. After 2 hours' stirring at −78° C., 2.5 ml of a saturated aqueous solution of NH$_4$Cl are slowly added and the reaction mixture is brought to room temperature. The precipitate is filtered off and washed copiously with tetrahydrofuran. The flitrate is concentrated in vacuo. The residue (dark-coloured meringue) is purified by chromatography on silica (CH$_2$Cl$_2$/ethyl acetate: 90/10) to yield 15 g of the expected product. Yield: 65 %

Step 3: Trans-2,3,5,6,7,8-hexahydro-8-hydroxy-7-(N-propylamino)naphtho[2,3-b]thiophene In a 500 ml three-necked flask fitted with a magnetic stirrer and a nitrogen inlet, 2.3 g (61 mmol) of AlLiH$_4$ are suspended in 75 ml of dry tetrahydrofuran. 6.2 g (24.5 mmol) of the product obtained in Step 2 dissolved in 97 ml of dry tetrahydrofuran are slowly added at room temperature. After 18 hours' stirring at room temperature, the reaction is stopped by the addition of 1.6 ml of water, 1.3 ml of 20 % NaOH in water and finally 5.8 ml of water in succession. The reaction mixture is stirred for 0.5 hour at room temperature and then filtered. The precipitate is washed copiously with tetrahydrofuran and the flitrate is concentrated in vacuo to yield 1.37 g of the expected product in the form of a meringue. Yield: 97 %.

Step 4: Trans-2,3,5,6,7,8-hexahydro-8-hydroxy-7-(N-propyl-N-chloroacetylamino)-naphtho-2,3-b]thiophene In a 2-liter three-necked flask fitted with a mechanical stirrer, 7.37 g (28 mmol) of the product obtained in Step 3 are dissolved in 420 ml of ethyl acetate. 420 ml of an aqueous 5% Na$_2$CO$_3$ solution and 3.34 ml (42 mmol) of chloroacetic acid chloride are added in succession at room temperature. After 0.5 hour's stirring at room temperature, the organic and aqueous phases are separated and the aqueous phase is extracted 3 times with ethyl acetate. The organic phases are combined, dried over magnesium sulphate and concentrated. The residue is purified by chromatography on silica (CH$_2$Cl$_2$/ethyl acetate: 90/10) to yield 6.69 g of the expected product in the form of a solid, M.p.(K): 162–164° C., Yield: 70 %.

Step 5: Trans-3,4,4a,5,6,8,9,11b-octahydrothieno [2,3 -b]-3-oxo-1,4oxazino [3,2-h]-4-propyl-2H-naphthalene In a 500 ml three-necked flask fitted with a magnetic stirrer and a nitrogen inlet 2 g (49.3 mmol) of NaH (60 % in oil, previously defatted by washing with penlane) are suspended in 37 ml of dry tetrahydrofuran. 6.96 g (19.7 mmol) of the product obtained in Step 4 dissolved in 97 ml of dry tetrahydrofuran and 27 ml of dry acetonitrile are slowly added at room temperature. After 6 hours' stirring at room temperature, the reaction is stopped by the slow addition of water while cooling the reaction mixture with a water-ice bath. The reaction mixture is taken up in H$_2$O (200 ml) and CH$_2$Cl$_2$ (100 ml), the phases are separated, and the aqueous phase is extracted three times with CH$_2$Cl$_2$ (50 ml each time). The organic phases are combined, washed with brine, dried over magnesium sulphate and concentrated to yield 5.86 g of the expected product in the form of a solid. M.p. (K): 168°–170° C., Yield: 98 %.

Step 6: Title product

In a 500 ml two-necked flask fitted with a magnetic stirrer, a condenser and a nitrogen inlet, 4.83 g (15.9 mmol) of the product obtained in Step 5 are dissolved in 182 ml of dry tetrahydrofuran. 15.9 ml (15.9 mmol) of borane-dimethyl sulphide [BH$_3$.S(CH$_3$)$_2$]are slowly added at room temperature. After 12 hours' stirring at reflux, the reaction is stopped by the slow addition of methanol while cooling the reaction mixture with a water-ice bath. After 0.5 hour's stirring at room temperature, the reaction mixture is concentrated in vacuo. The residue is taken up in 200 ml of methanol and heated at reflux for 1.5 hours in the presence of 1 ml of aqueous 37 % HCl, then concentrated in vacuo. The solid residue is taken up in 100 ml of ethyl ether and 100 ml of 1N sodium hydroxide solution. The aqueous phase is extracted four times with 60 ml of ethyl ether each time. The organic phases are combined, washed with brine, dried over magnesium sulphate and concentrated to yield 5.14 g of a thick oil. That residue is taken up in 100 ml of ethyl ether and the title product in the form of the hydrochloride (4.67 g, yield: 90 %) is precipitated by the addition of ethereal hydrogen chloride.

M.p.(K):>260° C. $^1$H NMR 200 MHz (CDCl$_3$/TMS), δ: 13.15 ppm (NH$^+$, unresolved peak exchangeable with D20); 7.3(s,IH); 6.9(s, 1H); 5.25 (d, 1H); 4.65(td, 1H); 4.15(dr, ill); 3.5(d, 1H); 3.2–3.4(m,SH); 2.7–3.1(m,SH); 2.3–2.6 (m,2H); 1.7–2.1(m,2H); 1.05(t,3H).

Example 3:

Trans-3,4,4a,5,6,8,9,11b-octahydro-10-oxothieno[2,3-b]-1,4-oxazino[3,2-h]-4-propyl-2H-naphthalene

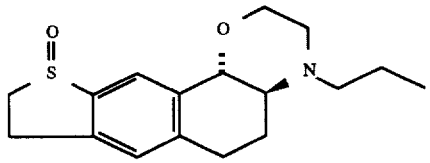

In a 250 ml two-necked flask fitted with a magnetic stirrer and a condenser, 3.56 g (10.9 retool) of the tire product of Example 2 in the form of the hydrochloride are dissolved in 77 ml of water. 5.5 ml of aqueous 1N HCl and 1.56 ml (13.75 mmol) of 30 % H20$_2$ are added in succession to that solution. The mixture is heated at 80° C. and stirred at that temperature for 0.5 hour. After returning to room temperature, the reaction mixture is rendered alkaline by the addition of 1N sodium hydroxide solution. The aqueous phase is extracted three times with 50 ml of ethyl ether each time. The organic phases are combined, washed with brine, dried over magnesium sulphate and concentrated to yield 3.57 g of a thick oil. That residue is purified by chromatography on silica (eluant: CH$_2$C12/methanol; 97/3) to yield 1.09 g of the less polar sulphoxide and 1.39 g of the more polar sulphoxide. Recrystallisation of each of the sulphoxides in 22 ml and 28 ml of ethyl acetate respectively makes it possible to obtain 0.62 g of the less polar sulphoxide and 0.87 g of the more polar sulphoxide, that is to say a total yield of 62 %.

Less polar sulphoxide : M.p.(MK): 170°–171° C. $^1$H NMR 400 MHz (DMSO d$_6$/TMS), δ: 7.75(s,1H); 7.3(s,1H); 4.25(d, 1H); 4.0–3.8(m,2H); 3.7–3.1(m,4H); 2.8(m,3H); 2.3 (m,3H); 2.05(m, 1H); 1.5(m,4H); 0.9(t,3H).

More polar sulphoxide : M.p.(MK): 169°–170° C. $^1$H NMR 200 MHz (DMSO d$_6$/TMS), δ: 7.75(s,1H); 7.3(s, 1H);

4.25(d, 1H); 4.0–3.8(m,2H); 3.7–3.1(m,4H); 2.8(m,3H); 2.3 (m,3H); 2.05(m, 1H); 1.5(m,4H); 0.9(t,3H).

Example 4:

Pharmacological study

The selectivity for $D_3$ receptors as compared with $D_2$ receptors has been demonstrated:

In vitro: by the $D_2$ and $D_3$ receptor binding technique

In vivo: by the capacity of the products of the invention to modulate hypothermia induced in the rat by the $D_3$ dopaminergic agonist: 7-OH-DPAT.

1. Material and method 1.1 In vitro-Binding

The affinity of the compounds of the invention for $D_3$ and $D_2$ receptors was determined on membrane preparations using [$^{125}$I]-iodosulpride as radioligand, raclopride (10 μM) determining the non-specific binding. The results are expressed as $IC_{50}$ values.

1.2 In vivo - Hypothermia in the rat

The tests were carded out on male Wistar rats weighing 200–250 g placed in individual cages with free access to food and water. The products were dissolved in distilled water to which several drops of lactic acid are added. The injections were effected in a volume of 1.0 ml/kg by the subcutaneous route. The doses are expressed in terms of the base. The rectal temperature of the rats was recorded using a digital thermistoprobe (Millan et al. I.P.E.T., 1993, 264, p. 1364–1376). During a first period, the rats were injected with the compound to be tested or the carrier, and were then put back in their cages for 30 minutes. The rats were then given an injection of 7-OH-DPAT (0.16 mg/kg) and were placed in their cages again. Thirty minutes later, the rectal temperature was measured and the difference was determined by comparison with the base values (ΔT° C.). The inhibitory dose (95 % confidence limits) for reducing the effect of the 7-OH-DPAT by 50 % was calculated according to the Finney method (Statistical Method in Biological Assays, 2nd ed., Hafner Publishing, New York, 1964).

2. Results 2.1 Binding

The affinities ($IC_{50}$) of the products of the invention for the $D_3$ receptor are from $10^{-9}$ M to $10^{-7}$ M, whilst those for the $D_2$ receptor are from 10-7 M to $10^{-5}$M.

2.2 Hypothermia in the rat

The effect of the products of the invention in respect of the $D_3$ receptor in vivo is illustrated by the behaviour of the compound of Example 2 in the hypothermia model. The values obtained in the course of that test are listed in the following Table:

| Injection 1 | Injection 2 | ΔT°C. (a) |
| --- | --- | --- |
| Carrier | Carrier | 0.53 ± 0.23 |
| Carrier | 7-OH-DPAT (0.16 mg/kg) | −1.66 ± 0.07 |
| Product of Example 2 0.16 mg/kg | 7-OH-DPAT (0.16 mg/kg) | −1.48 ± 0.44 |
| Product of Example 2 0.63 mg/kg | 7-OH-DPAT (0.16 mg/kg) | −0.18* ± 0.21 |
| Product of Example 2 2.5 mg/kg | 7-OH-DPAT (0.16 mg/kg) | 0.56* ± 0.26 |

(a) the values are the means ± sem n ≧ 5 per value
*p < 0.05 versus carrier/7-OH-DPAT according to Dunnett's test The inhibitory dose ($ID_{50}$) (95 % C.L.=95 % confidence limits) is 0.41 (0.19–0.87) mg/kg, s.c. which clearly demonstrates that the products of the invention not only recognise the $D_3$ receptor in vitro but act, in vivo, by the intermediary of that same $D_3$ receptor.

We claim:

1. A compound selected from the group consisting of those of formula I:

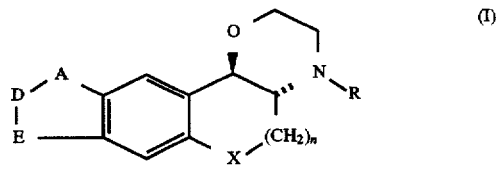

wherein:

—A—D—E— is selected from the group consisting of:

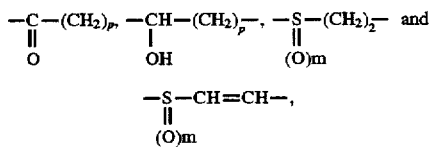

wherein:

p is selected from 2 and 3 and
m is selected from zero, 1, and 2;

X represents:
$CH_2$ and, in addition, when —A—D—E— is selected from

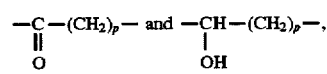

X may also represent oxygen;

n represents:
zero or 1 when X represents $CH_2$ and
solely 1 when X represents oxygen;

R is selected from the group consisting of:
hydrogen, and
($C_1$–$C_{10}$)alkyl, ($C_3$–$C_{10}$)alkenyl, ($C_3$–$C_{10}$)alkynyl, each in straight or branched chain and each unsubstituted or substituted by one or more cycloalkyl having 3 to 8 carbon atoms inclusive, or by aryl selected from phenyl, thienyl, and pyridyl, each of which is unsubstituted or substituted by one or more substituents selected from halogen, hydroxy, alkyl, and alkoxy each alkyl or alkoxy having 1 to 6 carbon atoms inclusive in straight or branched chain; which compounds have a trans ring junction between the 1,4-oxazine ring and the ring adjacent thereto, in racemic form or in the form of optical isomers,
and also addition salts thereof with a pharmaceutically-acceptable acid.

2. A compound of claim 1 which is selected from the group consisting of trans-3,4,4a,5,6,8,9,11b-octahydrothieno[2,3-b]-1,4-oxazino[3,2-h]-4-propyl-2H-naphthalene and its hydrochloride.

3. A method for treating a living animal body afflicted with a condition which is responsive to a product which binds to $D_3$ receptors, comprising the step of administering to the said living animal body an amount of a compound of claim 1 which is effective for alleviation of said condition.

4. A pharmaceutical composition useful for treating depression, comprising as active ingredient at least one of the compounds according to claim 1 together with one or more pharmaceutically acceptable excipients.

* * * * *

UNITED STATES PATENT AND TRADEMARK OFFICE
CERTIFICATE OF CORRECTION

PATENT NO. : 5,733,908
DATED : March 31, 1998
INVENTOR(S) : J.L. Peglion, B. Goument, J.C. Harmange, M. Millan, V. Audinot It is certified that error appears in the above-indentified patent and that said Letters Patent is hereby corrected as shown below:

Column 2, line 49: "figands" should read -- ligands --.

Column 6, line 10: "aluminjure" should read -- aluminium --.

Column 6, line 62: "mute" should read -- route --,

Column 8, line 8: "ethanolam" should read -- ethanolate --.

Column 8, line 35: In the two instances of "retool" each should read -- mmol --.

Column 8, line 40: "CH$_2$Cl2" should read -- CH$_2$Cl$_2$ --.

Column 8, line 50: "retool" should read -- mmol --.

Column 9, line 51: "flitrates" should read -- filtrates --.

Column 10, line 57: "propiOnylaminonaphtho[2,3-b]thi.ophene" should read -- propionylamino-naphtho[2,3-b]thiophene --.

Column 10, line 59: "retool" should read -- mmol --

UNITED STATES PATENT AND TRADEMARK OFFICE
CERTIFICATE OF CORRECTION

PATENT NO. : 5,733,908
DATED : March 31, 1998  Page 2 of 3
INVENTOR(S) : J.L. Peglion, B. Goument, J.C. Harmange, M. Millan, V. Audinot It is certified that error appears in the above-indentified patent and that said Letters Patent is hereby corrected as shown below:

Column 10, line 63: "retool" should read -- mmol --

Column 10, line 65: Delete "1o" after the word "room".

Column 11, line 9: "retool" should read -- mmol --

Column 11, line 16: "flitrate" should read -- filtrate --.

Column 11, line 32: "flitrate" should read -- filtrate --.

Column 11, line 53: "Nail" should read --NaH --.

Column 11, line 54: "penlane" should read -- pentane --.

Column 12, line 24: "D20);" should read -- $D_2O$); --

Column 12, line 25: At the end of the line, "(dr.ill);" should read -- (dd, 1H); --.

Column 12, line 26: In two instances, "(m,SH);" should read -- (m,5H); --.

UNITED STATES PATENT AND TRADEMARK OFFICE
CERTIFICATE OF CORRECTION

PATENT NO. : 5,733,908
DATED : March 31, 1998
INVENTOR(S) : J.L. Peglion, B. Goument, J.C. Harmange, M. Millan, V. Audinot It is certified that error appears in the above-indentified patent and that said Letters Patent is hereby corrected as shown below:

Column 12. line 43: "(10.9 retool) of the tire" should read -- (10.9 mmol of the title --.

Column 12, line 46: "H20$_2$" should read -- H$_2$O$_2$ --.

Column 12, line 55: "CH$_2$Cl2/" should read -- CH$_2$Cl$_2$/ --.

Column 14, line 47 (approx.): "and alkoxy each" should read -- and alkoxy, each --.

Column 14, line 65: Insert a -- - -- (dash) between "pharmaceutically" and "acceptable".

Signed and Sealed this

Thirtieth Day of June, 1998

Attest:

BRUCE LEHMAN

Attesting Officer   Commissioner of Patents and Trademarks